US00PP27273P2

(12) United States Plant Patent
Hooljman

(10) Patent No.: US PP27,273 P2
(45) Date of Patent: Oct. 18, 2016

(54) ROSE PLANT NAMED 'ESM R145'

(50) Latin Name: *Rosa hybrida*
Varietal Denomination: ESM R145

(71) Applicant: Aloysius A. J. Hooljman, Aalsmeer (NL)

(72) Inventor: Aloysius A. J. Hooljman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 183 days.

(21) Appl. No.: 14/121,559

(22) Filed: Sep. 17, 2014

(51) Int. Cl.
*A01H 5/02* (2006.01)

(52) U.S. Cl.
USPC ..... Plt./138

(58) Field of Classification Search
USPC ..... Plt./138
See application file for complete search history.

*Primary Examiner* — Keith Robinson
(74) *Attorney, Agent, or Firm* — C. A. Whealy

(57) ABSTRACT

A new and distinct cultivar of Rose plant named 'ESM R145', characterized by its upright and long flowering stems; vigorous growth habit and high productivity; dark green-colored leaves; dark pink-colored flowers that are held on strong pedicels on relatively large sprays; freely flowering habit; excellent postproduction longevity; and good tolerance to pathogens common to Rose plants.

1 Drawing Sheet

Botanical designation: *Rosa hybrida.*
Cultivar denomination: 'ESM R145'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R145'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in November, 2008 of a proprietary Rose selection identified as Line 90, not patented, as the female, or seed, parent with a proprietary Rose selection identified as Line 405, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in September, 2009.

Asexual reproduction of the new Rose plant by bud grafting in El Quinche, Pichincha, Ecuador since March, 2010 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R145'. These characteristics in combination distinguish 'ESM R145' as a new and distinct Rose plant:

1. Upright and long flowering stems.
2. Vigorous growth habit and high productivity.
3. Dark green-colored leaves.
4. Dark pink-colored flowers that are held on strong pedicels on relatively large sprays.
5. Freely flowering habit with typically about six to nine flowers per spray.
6. Excellent postproduction longevity.
7. Tolerant to pathogens common to Rose plants.

Plants of the new Rose differ from plants of the female parent selection in the following characteristics:

1. Plants of the new Rose have longer flowering stems than plants of female parent selection.
2. Stems of plants of the new Rose are more vigorous than plants of the female parent selection.
3. Plants of the new Rose and the female parent selection differ in flower color as plants of the female parent selection have light pink-colored flowers.

Plants of the new Rose differ from plants of the male parent selection in the following characteristics:

1. Plants of the new Rose are slightly shorter than plants of the male parent selection.
2. Stems of plants of the new Rose have more thorns than stems of plants of the male parent selection.
3. Plants of the new Rose and the male parent selection differ in flower color as plants of the male parent selection have pinkish orange-colored flowers.
4. Flowers of plants of the new Rose have more petals than flowers of plants of the male parent selection.

Plants of the new Rose can be compared to plants of *Rosa hybrida* 'Twinkle Bride', not patented. In side-by-side comparisons conducted in El Quinche, Pichincha, Ecuador, plants of the new Rose differed from plants of 'Twinkle Bride' in the following characteristics:

1. Plants of the new Rose were larger than plants of 'Twinkle Bride'.
2. Plants of the new Rose were more vigorous than plants of 'Twinkle Bride'.
3. Stems of plants of the new Rose had more thorns than stems of plants of 'Twinkle Bride'.
4. Plants of the new Rose had larger leaves and leaflets than plants of 'Twinkle Bride'.
5. Plants of the new Rose had larger sprays than plants of 'Twinkle Bride'.
6. Plants of the new Rose had stronger flower pedicels than plants of 'Twinkle Bride'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photographs on the left side of the sheet comprise side perspective and close-up views of typical flowering stems of 'ESM R145'.

The photograph at the upper right of the sheet is a close-up view of a typical developed flower of 'ESM R145'.

The photographs at the lower right of the sheet are close-up views of the upper and lower surfaces of typical leaves of 'ESM R145'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were 37 weeks old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R145'.

Parentage:

*Female, or seed, parent*.—Proprietary seedling selection of *Rosa hybrida* identified Line 90, not patented.

*Male, or pollen, parent*.—Proprietary seedling selection of *Rosa hybrida* identified Line 405, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Fine, fibrous; close to N199B in color.

*Rooting habit*.—Moderately freely branching; dense.

Plant description:

*Plant and growth habit*.—Perennial shrub; upright and strong flowering stems; typically grown as a spray-type cut flower; vigorous growth habit.

*Branching habit*.—Freely basal branching habit; highly productive with about 10.2 flowering stems developing per plant per year.

*Plant height*.—About 141 cm.

*Plant width (spread)*.—About 55 cm.

*Lateral branches*.—Quantity: Freely branching habit with about nine lateral branches developing per plant. Length: About 94 cm. Diameter: About 7.8 mm. Internode length: About 4.8 cm. Texture: Smooth, glabrous; older stems, woody. Color: Close to 146A and N199A. Thorns: Density: Medium. Shape: Triangular with sharp acuminate apices; slightly incurved and flat. Height: About 8 mm. Length, at base: About 9 mm. Color, immature: Close to 183C and 152A. Color, mature: Close to 153A and 34D.

Leaf description:

*Arrangement*.—Alternate; compound with typically seven leaflets per leaf.

*Leaf length*.—About 18.3 cm.

*Leaf width*.—About 10.9 cm.

*Terminal leaflet length*.—About 6 cm.

*Terminal leaflet width*.—About 4.2 cm.

*Lateral leaflet length*.—About 5.3 cm.

*Lateral leaflet width*.—About 3.8 cm.

*Leaflet shape*.—Ovate.

*Leaflet apex*.—Acuminate.

*Leaflet base*.—Rounded.

*Leaflet margin*.—Serrate.

*Leaflet texture, upper and lower surfaces*.—Smooth; papery to coriaceous.

*Leaflet venation pattern*.—Pinnate.

*Leaflet color*.—Developing leaflets, upper surface: Close to 139A. Developing leaflets, lower surface: Close to 147B. Fully expanded leaflets, upper surface: Close to between 139A and 147A; venation, close to 152A. Fully expanded leaflets, lower surface: Close to 147B; venation, close to 146C.

*Petioles, leaves*.—Length: About 2.3 cm. Diameter: About 2.1 mm. Texture, upper surface: Prickly. Texture, lower surface: Smooth, glabrous. Color, upper surface: Close to 146C and 172B. Color, lower surface: Close to 146A to 146D.

*Petioles, leaflets*.—Length: About 2.9 cm. Diameter: About 1.2 mm. Texture, upper surface: Prickly. Texture, lower surface: Smooth, glabrous. Color, upper surface: Close to 146A. Color, lower surface: Close to 146A to 146D.

*Stipules*.—Arrangement and appearance: Two, adnate to the petiole, leafy in appearance. Length: About 2.8 cm. Width: About 3.9 mm. Shape: Roughly deltoid. Apex: Acuminate, tapered. Base: Tapered. Margin: Serrate. Texture, upper and lower surfaces: Smooth; membranous. Venation pattern: Pinnate. Color, upper surface: Close to 137A. Color, lower surface: Close to 146A.

Flower description:

*Flower type and arrangement*.—Symmetrical rosette flowers; flowers typically grown as spray-types; flowers face upright; freely flowering with typically six to nine flowers per spray.

*Flowering season*.—Plants of the new Rose flower year-round under greenhouse conditions; early flowering habit, plants begin flowering about 78 days after pinching.

*Spray diameter*.—About 19.8 cm.

*Spray height*.—About 30 cm.

*Flower diameter*.—About 6.1 cm.

*Flower depth* (*height*).—About 3 cm.

*Flower longevity*.—Excellent postproduction longevity; flowers maintain good substance for about 28 days on the plant and for about ten days as cut flowers; flowers persistent.

*Fragrance*.—None detected.

*Flower buds*.—Length: About 3.1 cm. Diameter: About 2.4 cm. Shape: Ovoid. Rate of opening: About eight days. Color: Close to between 144A and 146A.

*Petals*.—Quantity: About 30 per flower; petals imbricate. Length: About 3.2 cm. Width: About 3.2 cm. Shape: Nearly round. Apex: Blunt to short acute. Base: Obtuse. Margin: Entire. Texture, upper and lower surfaces: Smooth, glabrous; papery to coriaceous. Color: When opening, upper surface: Close to 52A; towards the base, close to between 145C and 150D. When opening, lower surface: Close to 52B; towards the base, close to between 154D and 157B. Fully opened, upper surface: Close to 54B; towards the base, close to 157B. Fully opened, lower surface: Close to between 54B and 55C; towards the base, close to 157B.

*Petaloids*.—Quantity: About four; whorled. Length: Variable. Width: Variable. Shape: Irregularly shaped. Apex: Short acute. Base: Obtuse. Margin: Mostly uneven. Texture, upper and lower surfaces: Smooth, glabrous; papery to coriaceous. Color: When opening, upper and lower surfaces: Close to 46D and 154D. Fully opened, upper and lower surfaces: Close to 55B and 157A.

*Sepals*.—Quantity per flower: Typically five in a single whorl. Length: About 2.8 cm. Width: About 1 cm. Shape: Roughly deltoid. Apex: Tapered. Base: Truncate. Margin: Entire; glandular. Texture, upper and lower surfaces: Leathery; rugose, pubescent and glandular. Color: When opening, upper surface: Close to 146B to 146D. When opening, lower surface: Close to 146A to 146D. Fully opened, upper surface: Close to 146A and 145B. Fully opened, lower surface: Close to 146A to 146D.

*Pedicels*.—Length: About 3.6 cm. Diameter: About 3 mm. Strength: Strong. Angle: About 36° from vertical. Texture: Spiny and glandular. Color: Close to 146B and N199A.

*Reproductive organs*.—Stamens: Quantity: About 138 per flower. Anther length: About 2.2 mm. Anther shape: Reniform. Anther color: Close to 2D and 163B. Filament color: Close to 1C. Pollen amount: Abundant. Pollen color: Close to 163A. Pistils: Quantity: About 69 per flower. Pistil length: About 1.2 cm. Stigma shape: Broadly reniform. Stigma color: Close to 162A. Style length: About 9 mm. Style color: Close to 145C and 46A. Receptacle height: About 9 mm. Receptacle diameter: About 8 mm. Receptacle shape: Cup-shaped. Receptacle texture: Smooth, glabrous. Receptacle color: Close to 144A. Fruits: Length: About 1.9 cm. Diameter: About 1.7 cm. Texture: Smooth. Color: Close to 144A and N163A. Seeds: Quantity per fruit: About twelve. Length: About 6 mm. Diameter: About 5 mm. Texture: Smooth. Color: Close to 161B.

Pathogen & pest tolerance: Plants of the new Rose have been observed to have good tolerance to Powdery Mildew, Downy Mildew and *Botrytis*. Plants of the new Rose have not been observed to be tolerant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R145' as illustrated and described.

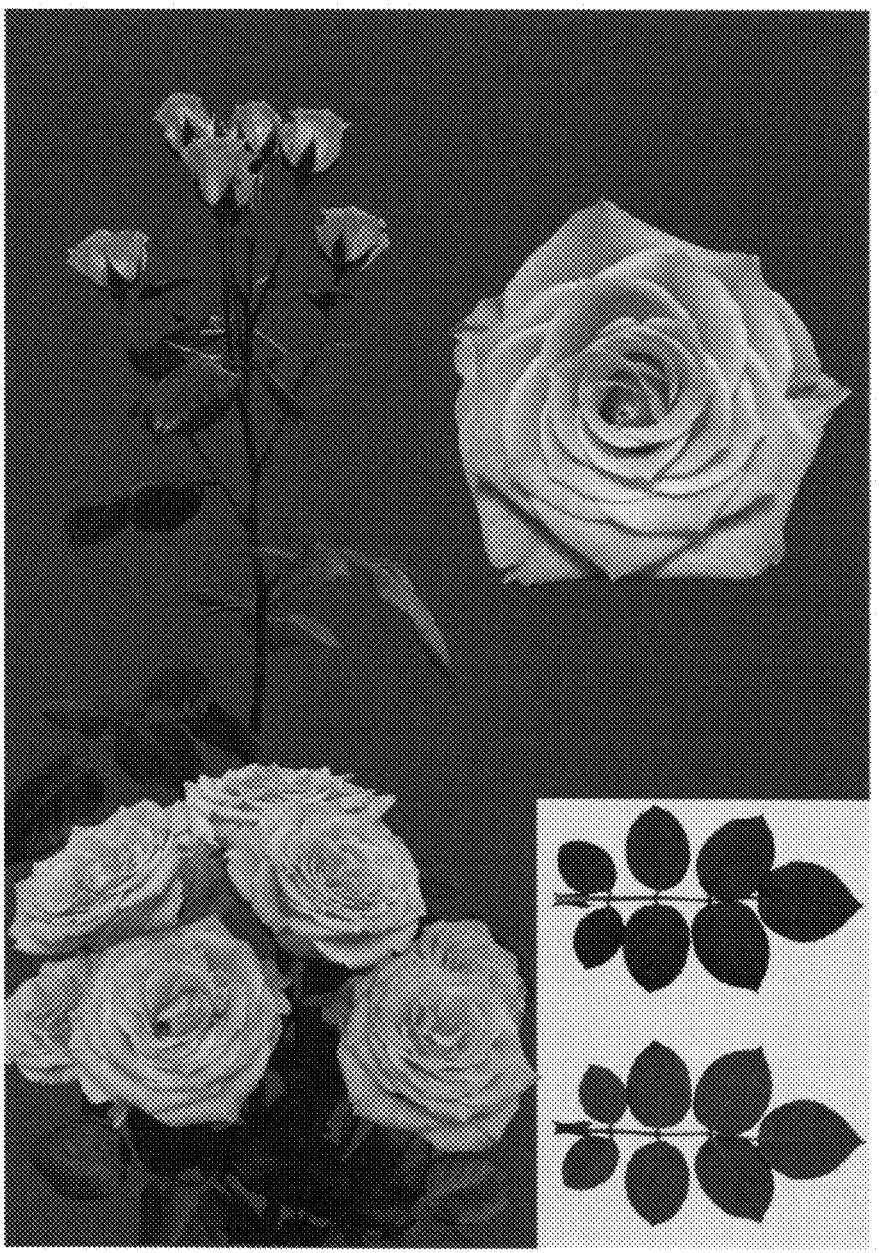

* * * * *